(12) United States Patent
Kiedrowski

(10) Patent No.: US 10,595,713 B2
(45) Date of Patent: Mar. 24, 2020

(54) OCULAR FOR A SURGICAL INSTRUMENT

(71) Applicant: OLYMPUS WINTER & IBE GMBH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 309 days.

(21) Appl. No.: 15/661,179

(22) Filed: Jul. 27, 2017

(65) Prior Publication Data
US 2017/0332885 A1 Nov. 23, 2017

Related U.S. Application Data

(63) Continuation of application No. PCT/EP2016/050752, filed on Jan. 15, 2016.

(30) Foreign Application Priority Data

Feb. 6, 2015 (DE) .......................... 10 2015 202 137

(51) Int. Cl.
*A61B 1/00* (2006.01)
*G02B 23/24* (2006.01)
*G02B 27/00* (2006.01)

(52) U.S. Cl.
CPC ........ *A61B 1/00195* (2013.01); *A61B 1/0011* (2013.01); *A61B 1/00137* (2013.01); *G02B 23/2453* (2013.01); *G02B 23/2476* (2013.01); *G02B 27/0018* (2013.01)

(58) Field of Classification Search
CPC ............ A61B 1/00126; A61B 1/00128; A61B 1/00195; A61B 1/00197; G02B 23/2476; G02B 23/2453

USPC ......................................... 600/112, 133, 137
See application file for complete search history.

(56) References Cited

U.S. PATENT DOCUMENTS 6,025,873 A 2/2000 Nishioka et al.
2013/0176395 A1* 7/2013 Kazakevich ....... A61B 1/00193
348/45
2013/0342906 A1 12/2013 Dahmen

FOREIGN PATENT DOCUMENTS

DE 4403566 A1 8/1995
DE 102012011717 A1 12/2013
JP S58-95317 A 6/1983
JP 58163917 U 11/1983
(Continued)

OTHER PUBLICATIONS

Japanese Office Action dated Dec. 25, 2018 in Japanese Patent Application No. 2017-541264.
(Continued)

*Primary Examiner* — Matthew J Kasztejna
(74) *Attorney, Agent, or Firm* — Scully, Scott, Murphy & Presser, P.C.

(57) ABSTRACT

An ocular device for a surgical instrument having an ocular mount for an optical assembly. The ocular device including: an optical flat; and a holder for accommodating the optical flat, wherein the holder is configured to be connected to the ocular mount; wherein the optical flat having a widened side edge provided with a first contact surface for the ocular mount and a second contact surface for the holder, and a surface normal of the optical flat and the first contact surface of the optical flat facing the ocular mount form an angle different than 0° relative to each other.

16 Claims, 2 Drawing Sheets

(56) References Cited

FOREIGN PATENT DOCUMENTS

JP          S60-15618  A      1/1985
JP          2002-357786 A    12/2002

OTHER PUBLICATIONS

International Search Report dated Apr. 12, 2016 issued in PCT/EP2016/050752.

\* cited by examiner

OCULAR FOR A SURGICAL INSTRUMENT

CROSS-REFERENCE TO RELATED APPLICATION

The present application is a continuation of PCT/EP2016/050752 filed on Jan. 15, 2016, which is based upon and claims the benefit to DE 10 2015 202 137.8 filed on Feb. 6, 2015, the entire contents of each of which are incorporated herein by reference.

BACKGROUND

Field

The present application relates to an ocular device for a surgical instrument, and in particular, to an endoscope or laparoscope, with an ocular mount for an optical assembly, wherein an optical flat is accommodated in a holder, and wherein the holder for the optical flat is connectible or connected to the ocular mount. Moreover, the present application relates to a surgical instrument, and in particular, to an endoscope or laparoscope.

Prior Art

Minimally invasive endoscopic surgery of the human or animal body is performed using endoscopes with a long or respectively elongated shaft that is introduced into an interior of or respectively a cavity in the body through a body opening existing or created for this purpose before surgery. Since the operative field in the body cavity cannot be viewed directly from the outside, known endoscopes enable a view of the body cavity to be treated. For this purpose, conventional endoscopes have an optical system with one or more lenses on the distal tip of the endoscope shaft that direct light from the body cavity into the endoscope. The endoscope shaft can have an arrangement of lenses such as rod lenses by means of which light is guided out of the body cavity to the proximal end of the endoscope, that is, to the end that is held and used by an operator or surgeon.

In the proximal region of the endoscope, for example, on a handle, there is an eyepiece with an ocular, that is, an optical system, from which the light entering the distal tip of the endoscope exits. Such an ocular can be used for direct observation with a naked eye brought up to the eyepiece.

SUMMARY

It is an object to enable a reflection-free detection of images by surgical instruments, such as by means of an image sensor unit, wherein the design complexity is minimized.

Such object can be achieved with an ocular device for a surgical instrument, such as an endoscope or laparoscope, with an ocular mount for an optical assembly, wherein an optical flat is accommodated in a holder, and wherein the ocular mount can be connected to the holder for the optical flat, which is configured such that a widened side edge of the optical flat is provided with a contact surface for the ocular mount and with a contact surface for the holder, wherein a surface normal of the optical flat and the contact surface of the optical flat facing the ocular mount form an angle different than 0°, such as an angle of between 2.0° and 10.0° aligned relative to each other, such as when the optical flat is accommodated in the holder.

With such ocular device for a surgical instrument, the surface normal of the optical flat which faces the ocular mount can be aligned at an angle unequal to 0° (i.e., ≠0°), i.e., not parallel to each other, relative to the optical axis is of the optical assembly accommodated in the ocular mount. Consequently, the entry side and the exit side, or respectively the surfaces of the optical flat, are aligned at an angle unequal to 0° relative to the perpendicular plane of the optical axis of the ocular device, whereby when light beams pass through the optical flat, or respectively the ocular glass, no reflections arise within the optical flat, and potential artifacts arising from (light) reflections in an image detection sensor are avoided.

Moreover, a contact surface on the ocular flat can be provided by arranging the ocular flat in the ocular mount by the widened side edge of the ocular flat which is perpendicular to the optical, or respectively mechanical axis of the ocular mount, or respectively the optical axis of the optical assembly of the ocular mount.

The optical flat can be configured as a flat ocular window for the ocular and has two parallel surfaces through which the light beams pass. The surfaces of the optical flat each have a corresponding surface normal which are perpendicular to the flat surface of the optical flat. The optical flat can be made of sapphire.

The optical flat which is provided as the ocular window can be configured with a peripheral widened side edge, wherein the contact surface for the ocular mount provided by the side edge is aligned at an angle to the surfaces of the optical flat which corresponds to the angle between the surface normal of the optical flat and the optical axis of the optical assembly accommodated in the ocular mount.

When arranging the optical flat on the ocular mount provided with an optical assembly, a flat contact shoulder can be formed for the optical flat, wherein the surfaces of the optical flat aligned parallel to each other are arranged oblique to the otherwise perpendicular alignment of the optical flat (according to the prior art). The widened side edge of the optical flat is formed in this context as a flat stop shoulder, wherein the flat stop shoulder is formed as a widened side edge at a sharp angle to one or both surfaces of the optical flat.

The surface normal or surface normals of the optical flat and the contact surface of the optical flat facing the ocular mount can be aligned at an angle between 4.0° to 8.0°, such as at an angle of 6° relative to each other. Correspondingly, the widened side edge of the optical flat with the contact surface for the ocular mount is formed at an angle of 4.0° to 8.0°, such as at an angle of 6°, e.g. to the surface at the distal entry side of the optical flat.

Moreover, the ocular device for the widened, peripheral side edge of the optical flat, or respectively the ocular glass, can be accommodated in a seat in the holder in a manner complementary to the shape and function. In one embodiment, the optical flat can be configured cylindrically.

The widened side edge of the optical flat can be configured like a ring.

To achieve a reliable connection between the ocular mount in which an optical assembly is accommodated and the holder, the holder can be configured as a union nut, which may be provided with an inner thread. The holder provided as a union nut with an inner thread can mate with an outer thread on the ocular mount. The optical assembly accommodated in the ocular mount can have one or more lenses and possibly additional optical elements.

In addition, the holder can be formed from plastic, wherein the holder, when designed as a union nut, can have an inner bevel which fits the optical flat and covers and compensates a projection of the optical flat or respectively ocular glass.

In addition, the holder, such as the union nut, can be configured with a recess in the side facing away from the optical flat. The recess formed in the proximal side achieves a flush connection with the angled optical flat, or respectively ocular glass, whereby soiled edges, etc. between the optical flat and holder are avoided on the proximal light exiting side.

The side of the optical flat facing away from the ocular mount, i.e., the proximal side, can be aligned flush with the region surrounding the optical flat, or the edge region of the holder, such as with the edge region of the recess of the holder surrounding the optical flat.

In addition, an eyepiece can be arranged on the holder of the ocular device. Such eyepiece can, for example, be screwed to the housing for the ocular mount, wherein the eyepiece is adapted on the inside to the holder, or respectively the union nut, and can moreover be configured with a groove for a radial seal (such as for an O-ring).

In addition, such object can be achieved with a surgical instrument, such as an endoscope or laparoscope that is configured with an above-described ocular device having any of the above configurations. When using such ocular device, reflections from the optical flat are avoided when imaging with an image sensor device, as well as ghost images from reflections by the ocular window or the proximal optical flat of the ocular.

BRIEF DESCRIPTION OF THE DRAWINGS

Further features will become apparent from the description of embodiments together with the claims and the included drawings. Embodiments can fulfill individual characteristics or a combination of several characteristics.

The embodiments will be described below, without restricting the general idea of the invention, based on exemplary embodiments in reference to the drawings, wherein we expressly refer to the drawings with regard to the disclosure of all details that are not explained in greater detail in the text.

In the drawings, the same or similar types of elements and/or parts are provided with the same reference numbers so that a reintroduction is omitted.

DETAILED DESCRIPTION

Figure 1:
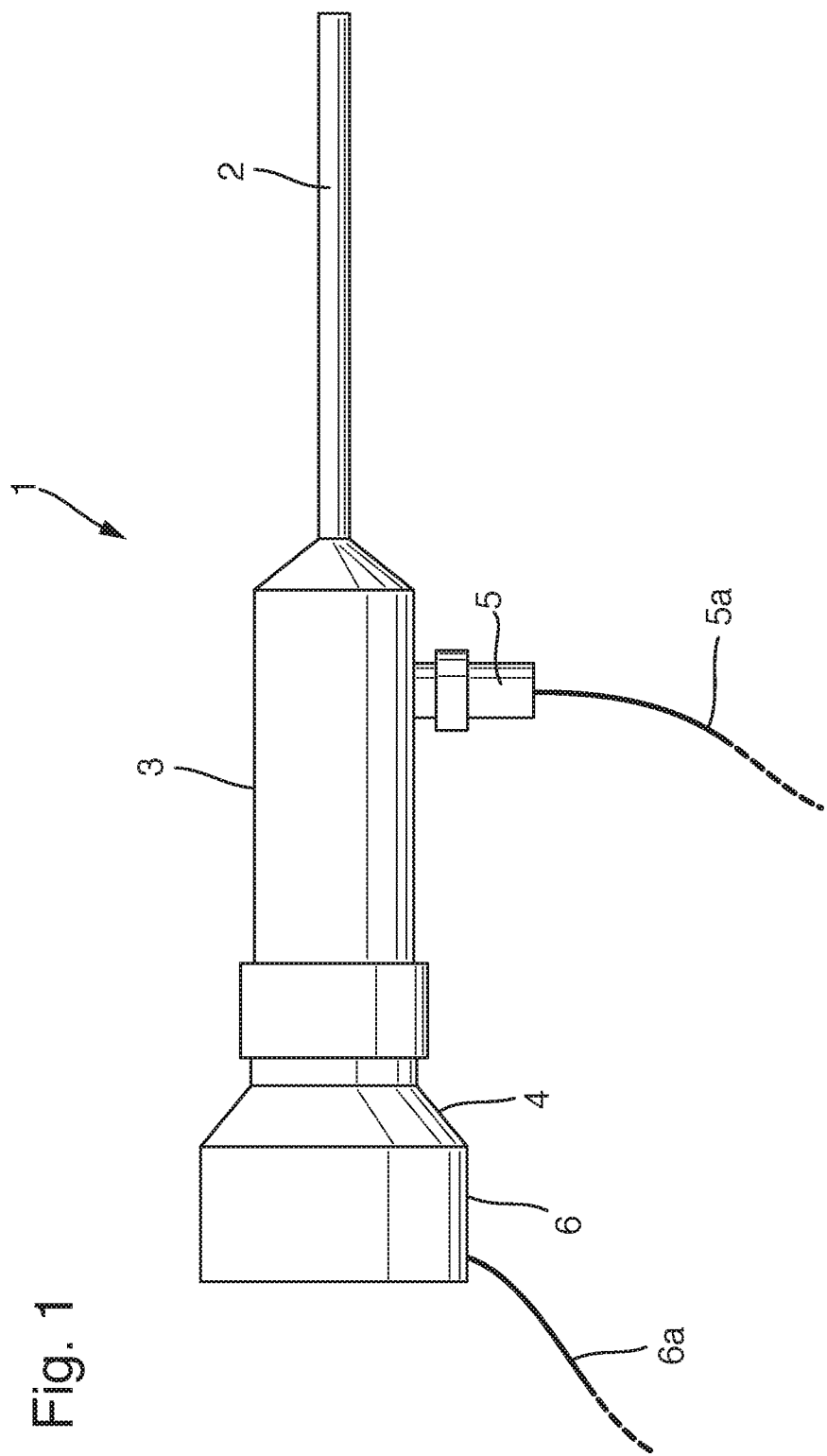
FIG. 1 illustrates a schematic side view of an endoscope.

FIG. 1 shows a schematic side view of an endoscope 1 that, at the distal end, has a tubular shaft 2 with an optical system. During minimally invasive surgery or a minimally invasive examination, this tubular shaft 2 is introduced through an opening in the body into a body cavity. The tubular shaft 2 opens into a housing 3 that in turn, on the proximal end, that is, on the end which is arranged toward the surgeon or operator, opens into an eyepiece 4 having an ocular, not shown. The housing 3 also serves for handling the endoscope 1.

On the side of the housing 3 of the endoscope 1, a light source 5, such as an LED light source, is arranged which introduces bright light from the side into the optical system of the endoscope 1, from where the introduced light exits at the distal end, that is, at the tip of the tubular shaft 2 in order to illuminate an is operative field. The light source 5 has a connection cable 5a. In the case of a customary optical system, the light source 5 can be an adapter to which a glass fiber bundle is attached as a connection cable 5a. The light delivered through the glass fiber bundle is then introduced into the endoscope 1 by means of the adapter. In an alternative version, there is an active light source 5, for example on the basis of LEDs, halogen luminaries or the like, wherein in this case, the connection cable 5a is a current supplying cable.

A schematically represented camera head 6 having an ocular adapter, not shown, is arranged at the eyepiece 4 of the endoscope 1 and captures the light exiting from the ocular of the endoscope 1 using its own optical system, and focuses the light on an optical area sensor, for example, a CCD chip. By means of the connector 6a for the camera head 6, the camera head 6 is supplied with current, image signals from the area sensor are transferred to an external evaluation unit, and control signals are transferred to the camera head 6.

Figure 2:
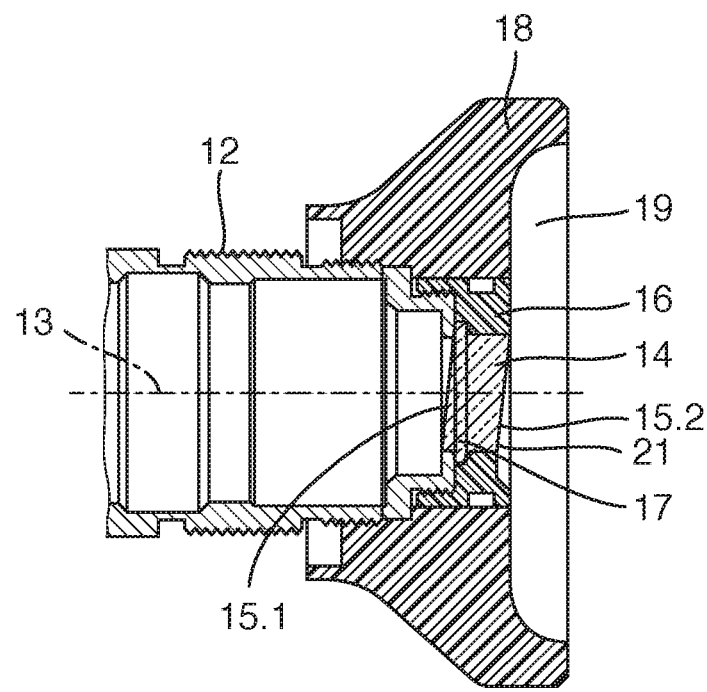
FIG. 2 schematically illustrates a cross-section of an ocular of an endoscope in a section, and FIG. 3 schematically illustrates a side view of an optical flat designed as an ocular window.

FIG. 2 schematically shows a cross-section of an ocular in a section at the proximal-side in the endoscope. The ocular has an ocular mount 12 in which for example imaging lenses (not shown) are arranged as an optical assembly. The ocular has an optical axis 13 of the optical assembly.

At the proximal end of the ocular mount 12 which is also termed an ocular window mount, an optical flat 14 is arranged as an ocular window which is accommodated in a union nut 16 provided with a recess. The union nut 16 has an inner thread which interacts with an outer thread of the ocular mount 12. In addition, an eyepiece 18 is arranged at the proximal side of the endoscope on the ocular mount 12 and has an eyepiece recess 19.

The optical flat 14 held by the union nut 16 has a light entry side 15.1 and a light exit side 15.2 which are aligned parallel to each other. The light entry side 15.1 and the light exit side 15.2 are aligned at an angle$\neq 90°$ relative to the optical axis 13. The optical axis 13 is co-linear with the mechanical axis of the ocular.

In order to align the surface normal of the optical flat 14 at an angle of 6° relative to the optical axis, the optical flat 14 has a retaining shoulder 17. A flat surface for contacting the proximal opening of the ocular mount 12 is provided by the peripheral retaining shoulder 17 as a flat contact shoulder. The retaining shoulder 17 in this case is aligned at an angle of 6° relative to the plane of the light entry side 15.1, or respectively to the light exit side 15.2 of the optical flat 14. The surface normals of the parallel light entry side 15.1 and light exit side 15.2 of the optical flat 14 are consequently aligned at an angle of 6° relative to the optical axis 13.

Figure 3:
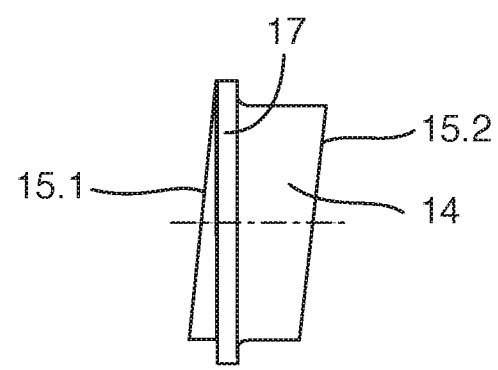

FIG. 3 schematically portrays an enlarged view of the optical flat 14.

The contact shoulder of the retaining shoulder 17 facing the ocular mount 12 is a flat surface in this case which is aligned perpendicular to the optical axis 13, or respectively the mechanical axis of the ocular mount. In this case, the proximal contact surface of the retaining shoulder 17 is arranged in a recess of the union nut 16 with a complementary shape.

The union nut 16 can be formed of plastic and moreover can have an inner bevel formed on the light exit side 15.2 of the optical flat 14, whereby the union nut 16 has a recess 21 on the proximal side. The union nut 16 is configured on the proximal side such that the recess 21 is aligned flush with the region bordering the optical flat 14 and the proximal surface, i.e., the light exit side 15.2 of the optical flat 14. Given the flush alignment of the proximal light exit side 15.2 of the optical flat 14 with the edge region of the recess 21 bordering and surrounding the optical flat 14, a transition free of interfering edges is formed between the edge of the optical flat 14 and the recess 21, whereby a jump in height between the optical flat 14 and the recess 21 surrounding the optical flat 14 is avoided.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

1 Endoscope
2 Tubular shaft with optical system
3 Housing
4 Eyepiece
5 Light source
5a Connection cable for the light source
6 Camera head
6a Connection for the camera head
12 Ocular mount
14 Optical flat
15.1 Light entry side
15.2 Light exit side
16 Union nut
17 Retaining shoulder
18 Eyepiece
19 Eyepiece recess
21 Recess

What is claimed is:

1. An ocular device for a surgical instrument having an ocular mount for an optical assembly, the ocular device comprising:
    an optical flat; and
    a holder for accommodating the optical flat, wherein the holder is configured to be connected to the ocular mount;
    wherein the optical flat having a shoulder extending from a circumferential surface of the optical flat, the shoulder having a first contact surface for the ocular mount and a second contact surface for the holder,
    a first direction normal to one of a light entry surface or light exit surface of the optical flat and a second direction normal to the first contact surface of the optical flat facing the ocular mount form an angle different than 0° relative to each other, and
    the circumferential surface of the optical flat extends in the second direction normal to the first contact surface.

2. The ocular device according to claim 1, wherein the angle is in a range between 2.0° and 10.0°.

3. The ocular device according to claim 1, wherein the angle is in a range between 4.0° to 8.0°.

4. The ocular according to claim 1, wherein the angle is 6°.

5. The ocular device according to claim 1, wherein the shoulder is configured to be accommodated in a seat in the holder, a shape of the shoulder corresponding to a shape of the seat.

6. The ocular device according to claim 1, wherein the shoulder of the optical flat is configured to have a ring shape.

7. The ocular device according to claim 1, wherein the shoulder is arranged on a periphery of the optical flat.

8. The ocular device according to claim 1, wherein the holder is configured as a union nut.

9. The ocular device of claim 8, wherein the holder comprises a thread on an inner surface of the holder.

10. The ocular device according to claim 1, wherein the holder is formed of plastic.

11. The ocular device according to claim 1, wherein the holder having a recess in the side facing away from the optical flat.

12. The ocular device according to claim 11, wherein a side of the optical flat facing away from the ocular mount is aligned flush with a region surrounding the optical flat.

13. The ocular according to claim 12, wherein the region surrounding the optical flat is an edge region of the recess surrounding the optical flat.

14. The ocular device according to claim 1, further comprising an eyepiece arranged on the holder.

15. A surgical instrument comprising the ocular device according to claim 1.

16. The surgical instrument according to claim 15, wherein the surgical instrument is one of an endoscope and laproscope.

* * * * *